US012064404B2

(12) United States Patent
Alur et al.

(10) Patent No.: US 12,064,404 B2
(45) Date of Patent: Aug. 20, 2024

(54) TOPICAL FORMULATIONS AND TREATMENTS

(71) Applicant: TRILOGIC PHARMA LLC, Tallassee, AL (US)

(72) Inventors: Hemant H. Alur, Tallassee, AL (US); James A H Harwick, Tallassee, AL (US)

( * ) Notice: Subject to any disclaimer, the term of this patent is extended or adjusted under 35 U.S.C. 154(b) by 0 days.

(21) Appl. No.: 17/903,489

(22) Filed: Sep. 6, 2022

(65) Prior Publication Data
US 2023/0093154 A1 Mar. 23, 2023

Related U.S. Application Data

(63) Continuation of application No. 16/504,290, filed on Jul. 7, 2019, now Pat. No. 11,458,113, which is a continuation of application No. 15/728,024, filed on Oct. 9, 2017, now Pat. No. 10,383,833.

(60) Provisional application No. 62/407,598, filed on Oct. 13, 2016.

(51) Int. Cl.
| | |
|---|---|
| A61K 9/06 | (2006.01) |
| A61B 17/32 | (2006.01) |
| A61K 9/00 | (2006.01) |
| A61K 31/167 | (2006.01) |
| A61K 47/34 | (2017.01) |
| A61K 47/36 | (2006.01) |
| A61L 26/00 | (2006.01) |

(52) U.S. Cl.
CPC .......... *A61K 31/167* (2013.01); *A61B 17/32* (2013.01); *A61K 9/0014* (2013.01); *A61K 9/06* (2013.01); *A61K 47/34* (2013.01); *A61K 47/36* (2013.01); *A61L 26/00* (2013.01); *A61B 2017/320004* (2013.01)

(58) Field of Classification Search
None
See application file for complete search history.

(56) References Cited

U.S. PATENT DOCUMENTS

| | | | |
|---|---|---|---|
| 4,529,601 A | 7/1985 | Broberg et al. | |
| 4,562,060 A | 12/1985 | Broberg et al. | |
| 5,993,836 A | 11/1999 | Castillo et al. | |
| 10,383,833 B2 | 8/2019 | Alur | |
| 2003/0077332 A1 | 4/2003 | Godfrey | |
| 2003/0198687 A1 | 10/2003 | Bennet | |
| 2010/0324110 A1 * | 12/2010 | Alur | A61K 47/36 514/422 |
| 2011/0257239 A1 | 10/2011 | Shah et al. | |
| 2013/0096064 A1 | 4/2013 | Chandler | |
| 2013/0131166 A1 | 5/2013 | Alur et al. | |

FOREIGN PATENT DOCUMENTS

| | | |
|---|---|---|
| WO | 2009/073658 A1 | 6/2009 |
| WO | 2011/153334 A2 | 12/2011 |
| WO | 2016079538 A1 | 5/2016 |
| WO | WO-2016079538 A1 * | 5/2016 |

OTHER PUBLICATIONS

Lok, et al. "EMLA cream as a topical anesthetic for the repeated mechanical debridement of venous leg ulcers: A double-blind, placebo-controlled study", Journal of the American Academy of Dermatology, 1999;40(2) Part 1:208-213.
Powers, et al., "Wound healing and treating wounds: Chronic wound care and management", Journal of the American Academy of Dermatology, 2016;74(4);607-625.
Overall Numbers Diabetes and Prediabetes; http://www.diabetes.org/diabetes-basics/statistics/; Jul. 2017.
Pontani, et al. Ten Patients with Painful Deep Wounds Evaluate Pain with Application of 2% Lidocaine Jelly Versus Regenecare® Wound Gel with 2% Lidocaine During Dressing Change; 22nd Annual Symposium on Advanced Wound Care and Wound Healing Society, Apr. 2009.
Phillips T., et al., "A study of the impact of leg ulcers on quality of life: financial, social, and psychologic implications." J Am Acad Dermatol. Jul. 1994;31(1):49-53.
Terry Treadwell, MD., et al., "Treatment of Pain in Wounds with a Topical Long Acting Lidocaine Ointment." 2014 (abstract).
Price PE, Fagervik-Morton H, Mudge EJ, et al., "Dressing-related pain, in patients with chronic wounds: an international patient perspective." Int Wound J., 2008;5(2):159-171.
Woo KY, Coutts PM, Price P, Harding K, Sibbald RG., "A randomized crossover investigation of pain at dressing change comparing 2 foam dressings." Adv Skin Wound Care. 2009;22(7):304-310.
S. Berger; What is the Difference between Lidocaine and Benzocaine? wiseGEEK; http://www.wisegeekhealth.com/what-is-the-difference-between-lidocaine-and-benzocaine.htm; Sep. 2017.

(Continued)

*Primary Examiner* — Brian Gulledge
(74) *Attorney, Agent, or Firm* — Clark G Sullivan

(57) ABSTRACT

The present invention provides topical dosages and formulations of lidocaine and pharmaceutically acceptable salts thereof, which are efficacious, chemically stable and physiologically balanced for safety and efficacy, particularly for debridement pain, and increase the duration of pain relief, and thereby provide more effective treatment to chronic open wounds, particularly those in non-mucosal tissue.

11 Claims, 2 Drawing Sheets

(56) References Cited

OTHER PUBLICATIONS

Stephanie Chandler; Lidocaine Vs. Benzocaine; http://www.ehow.com/about_5398369_lidocaine-vs-benzocaine.html; 2017.
Michael F. Powell, "Stability of Lidocaine in Aqueous Solution: Effect of Temperature, pH, Buffer, and Metal Ions on Amide Hydrolysis", Pharmaceutical Research, Feb. 1987;4(1):42-45.
Astero hydrogel topical anesthetic, drug information, dosage and strength, instructions and usage, side effects; Gensco Laboratories, Mar. 1, 2017.
International Search Report and Written Opinion issued in corresponding International Application No. PCT/US17/55749 on Nov. 29, 2017.

\* cited by examiner

TOPICAL FORMULATIONS AND TREATMENTS

FIELD OF THE INVENTION

The present invention relates to topical dosage forms and formulations of lidocaine. These formulations are therapeutically effective for inducing local anesthesia, chemically stable, and particularly useful for the relief of debridement pain of chronic open wounds.

BACKGROUND OF THE INVENTION

In the Unites States chronic wounds affect the nation's population and health care costs. It has been estimated that more than six million people suffer from chronic wounds, deriving from decubitus, vascular, inflammatory, and rheumatologic sources. The number of such people is expected to increase due to the growth in the elderly population and the prevalence of diabetes in such population. Concurrently, the growing population with chronic wounds leads to an increase in medical costs as evidenced by a study showing that chronic wound care cost $9.7 billion in 2004. Therefore, an improvement of chronic wound treatment in medical procedures would address a number of social and medical issues.

One of the problems accompanying chronic wound treatment is associated with pain that a patient may suffer. It has been found that up to 69% of patients with chronic venous ulcers suffer significant pain. Pain may be even more severe for patients suffering from an underlying disease process such as diabetic peripheral neuropathy.

For appropriate pain management in patients with chronic wounds, it is necessary to determine the source of the pain, i.e., whether the pain arises from the wound itself or from the underlying disease. If the pain is due to the wound itself, treatment of the wound with moisture retentive wound dressings, controlling infection, assuring adequate circulation, and reducing edema are a typical protocol to relieve the pain. If the pain is associated with an underlying disease such as diabetes mellitus, successful pain management requires special care as well as primary care since pain is often worsened by wound treatments, such as dressing changes as well as vulnerable periwound skin. In fact, one study showed that it was a major concern for 43% of medical practitioners to control acute pain during wound debridement. Another study confirmed that wound treatments themselves such as dressing removal, debridement, and inappropriate dressing selection promote wound related pain. Therefore, it is necessary to use analgesics or anesthetics during wound treatments.

Analgesics are categorized into two types, narcotics and non-narcotics, and are frequently used for long-term pain relief in patients with chronic wounds. However, the long-term use of either narcotics or non-narcotic can lead to tolerance and necessity of dose escalation. The former leads to addiction, dependence and tolerance while the latter causes a ceiling effect.

Topical anesthetics are widely used to numb the skin and to relive pain in medical and surgical procedures in anesthesia, ophthalmology, otorhinolaryngology, dentistry, urology, and aesthetic surgery. Among topical anesthetics, lidocaine, tetracaine, benzocaine, and prilocaine in a cream, ointment, or gel are commonly available prescription and/or over-the-counter (OTC) topical anesthetics.

Of the anesthetics, both lidocaine and benzocaine are most popular and commonly used in medical procedures. Lidocaine absorbs more quickly where applied due to its higher water-solubility and tends to last longer than benzocaine. Thus, benzocaine is often found in sunburn and oral ulcer products whereas lidocaine is more often found in prescription medications. Unfortunately, lidocaine is most effectively absorbed through mucosal surfaces, not skin.

Lidocaine HCl has been used in topical dosage forms for topical anesthesia in mucosal tissues and could be attractive, particularly if it is used as a topical anesthetic in non-mucosal tissues to reduce the debridement pain arising from chronic open wounds.

For example, compositions and methods for treating a disease, such as infection, pain or inflammation are reported in PCT International Publication No. WO 2011/153334 to Trilogic Pharma LLC. The composition comprises water, polyethylene glycol and/or ethyl alcohol, poloxamer, xanthan gum and active ingredients. Among various active ingredients, benzocaine is preferably used since it provides a superior degree of pain relief or analgesia for an extended period of time. The composition is implanted into a bodily cavity or applied to a tissue or oral mucosa.

Compositions and methods for delivering a drug for preventing bacterial infections are reported in PCT International Publication No. WO 2009/073658 to Trilogic Pharma LLC. The composition comprises water, copolymer, xanthan gum and an antibiotic, an anesthetic, or an analgesic. The composition is implanted into open cavities of human tissue including periodontal pockets, surgical incisions and open wounds.

Compositions and methods for preparing a local anesthetic in base form in order to obtain topical anesthesia through skin are reported in U.S. Pat. No. 4,529,601 to Astra Lakemedel Aktiebolag and U.S. Pat. No. 4,562,060 to Astra Lakemedel Aktiebolag (EMLA® cream). The composition comprises a mixture of lidocaine and prilocaine in the form of its base in a weight ratio of 1:1 (2.5% and 2.5%) with purified water (92%), which delivers the topical anesthetic through the skin. However, it takes at least 60 minutes for the anesthetic to take effect and an occlusive dressing after an application of the cream is necessary.

Fast acting compositions of topical transdermal anesthetics are reported in U.S. Pat. No. 5,993,836 to Castillo. The composition comprises a eutectic mixture of lidocaine and prilocaine in a weight ratio of about 3:1 in a lipophilic base. The composition takes effect in as little as 10-40 minutes without occlusive dressing for incision, excision, ablation, vaporization and coagulation of body soft tissues in medical specialties including aesthetic (dermatology and plastic surgery), podiatry, otolaryngology (ENT), gynecology, neurosurgery, arthroscopy (knee surgery) and invasive and endoscopic general surgery. The average desensitization period of the composition is 180 minutes.

Despite these existing treatments as indicated above there remains a need for topical anesthetics, particularly for use in chronic open wounds to reduce the debridement pain. Accordingly, it is an object of the present invention to provide a topical anesthetic which reduces the debridement pain. Another object of the present invention is to provide a topical anesthetic which exhibits a consistent anesthetic effect with no significant patient to patient variability. Yet another object of the present invention is to provide a topical anesthetic which has a predictable duration of anesthetic effect.

SUMMARY OF THE INVENTION

After extensive research and experimentation, the inventors have unexpectedly discovered that by formulating a topical anesthetic into a poloxamer gel/jelly base, they can reduce debridement pain, increase the duration of pain relief, potentially reduce the frequency of narcotic analgesic need, and thereby provide more effective treatment to chronic open wounds, particularly those in non-mucosal tissue. Surprisingly, they have discovered that slowing the release of lidocaine from their gel or ointment, using a poloxamer of the present invention, provides the same relief as more quickly releasing formulations, and for longer periods of time.

Thus, in a first principal embodiment, the invention provides a method of treating pain comprising applying to an open wound a topical dosage form comprising from 2 to 5% lidocaine, wherein said dosage form releases less than 75% of its lidocaine at 30 minutes and less than 90% of its lidocaine at 60 minutes when tested in a USP Apparatus 1 (paddle) at 50 rpm in 500 ml of an acetic acid/sodium acetate buffer, pH 4.0 at 32° C.

In a second principal embodiment the invention provides a method of treating debridement pain in a chronic open wound in non-mucosal tissue, comprising: (a) debriding the chronic open wound; (b) topically applying to the chronic open wound a gel/jelly comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— [CH$_2$—CH$_2$—O]$_a$— [CH$_2$—CH(CH$_3$)—O]$_b$— [CH$_2$—CH$_2$—O]$_a$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of an anesthetic; (c) applying an occlusive bandage to the chronic open wound; (d) removing the occlusive bandage from the chronic open wound; and (e) debriding the chronic open wound.

In a third principal embodiment, the invention provides a method of more generally treating pain in a chronic open wound in non-mucosal tissue in a patient in need thereof, comprising topically applying to the chronic open wound a gel/jelly comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— [CH$_2$—CH$_2$—O]$_a$— [CH$_2$—CH(CH$_3$)—O]$_b$— [CH$_2$—CH$_2$—O]$_a$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of an anesthetic.

Additional advantages of the invention are set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description serve to explain the invention.

DETAILED DESCRIPTION

Definitions and Use of Terms

Figure 1:
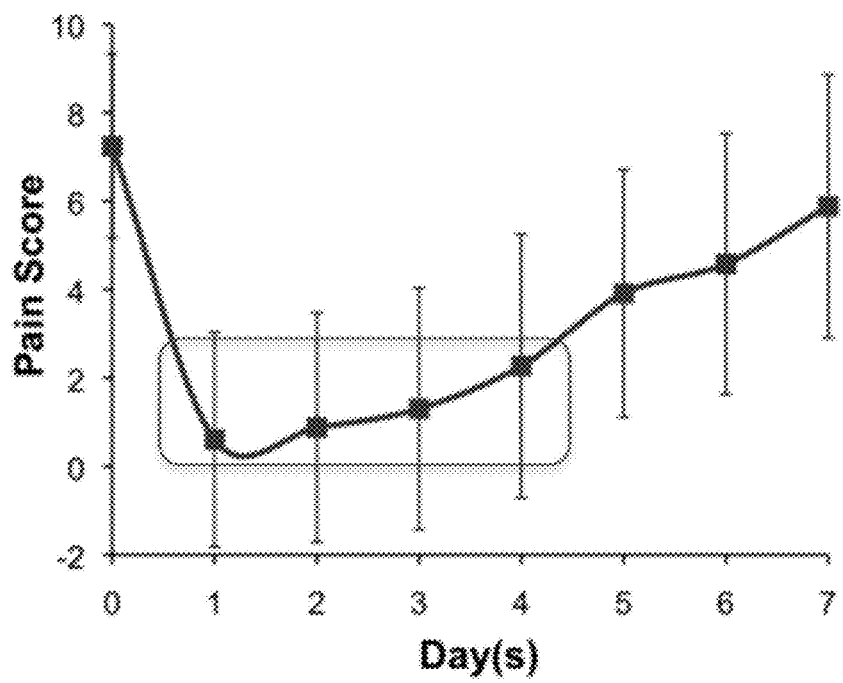
FIG. 1 shows the change in Numeric Rating Scale (NRS) pain scores reported by patients participating in an experiment of Example 2 over one week after the application of lidocaine gel in TRI-726 matrix (MP-601gel).

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

As used in the specification and claims, the singular forms a, an, and the include plural references unless the context clearly dictates otherwise. For example, the term "a pharmaceutically acceptable salt" refers to one or more pharmaceutical acceptable salts for use in the presently disclosed formulations and methods.

When used herein the term "about" will compensate for variability allowed for in the pharmaceutical industry and inherent in pharmaceutical products, such as differences in product strength due to manufacturing variation and time-induced product degradation. In one embodiment the term allows for any variation which in the practice of pharmaceuticals would allow the product being evaluated to be considered pharmaceutically equivalent or bioequivalent to the recited strength. In another embodiment the term allows for any variation within 5% of the recited strength or concentration of the formulation.

The terms "treating" and "treatment," when used herein, refer to the medical management of a patient with the intent to cure, ameliorate, stabilize, or prevent a disease, pathological condition, injury, or disorder (collectively "disorder"). This term includes active treatment, that is, treatment directed specifically toward the improvement of a disorder, and also includes causal treatment, that is, treatment directed toward removal of the cause of the associated disorder. In addition, this term includes palliative treatment, that is, treatment designed for the relief of symptoms rather than the curing of the disorder; preventative treatment, that is, treatment directed to minimizing or partially or completely inhibiting the development of the disorder; and supportive treatment, that is, treatment employed to supplement another specific therapy directed toward the improvement of the disorder.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use. "Pharmaceutically acceptable salts" means salts that are pharmaceutically acceptable, as defined above, and which possess the desired pharmacological activity.

When a weight of an active ingredient is given without reference to the free base or salt of the active ingredient, it will be understood that the weight can refer to the weight of the free base or the weight or the entire salt. In like manner, when the molecule can exist as a hydrate, and the weight of the molecule is given, it will be understood that the weight refers to the weight of the molecule without the waters of hydration.

When ranges are expressed herein by specifying alternative upper and lower limits of the range, it will be understood that the endpoints can be combined in any manner that is mathematically feasible. Thus, for example, a range of from 50 or 80 to 100 or 70 can alternatively be expressed as a series of ranges of from 50 to 100, from 50 to 70, and from 80 to 100. When a series of upper bounds and lower bounds are related using the phase and/or, it will be understood that the upper bounds can be unlimited by the lower bonds or combined with the lower bounds, and vice versa. Thus, for example, a range of greater than 40% and/or less than 80% includes ranges of greater than 40%, less than 80%, and greater than 40% but less than 80%.

When percentages, concentrations or other units of measure are given herein, it will be understood that the units of measure are weight percent unless otherwise stated to the contrary.

Mucosal tissues are defined groups of very similar cells gathered together to cover the inside surface of parts of the body such as the nose and mouth and to produce mucus to protect them. Thus, non-mucosal tissues refer to tissues which do not satisfy the above definition such as skin.

Discussion of Principal Embodiments

The invention can be defined based on several principal embodiments which can be combined in any manner physically and mathematically possible to create additional principal embodiments.

In a first principal embodiment, the invention provides a method of treating pain comprising applying to an open wound a topical dosage form comprising from 2 to 5% lidocaine, wherein said dosage form releases less than 75% of its lidocaine at 30 minutes and less than 90% of its lidocaine at 60 minutes when tested in a USP Apparatus 1 (paddle) at 50 rpm in 500 ml of an acetic acid/sodium acetate buffer, pH 4.0 at 32° C.

In a second principal embodiment the invention provides a method of treating a debridement pain in a chronic open wound in non-mucosal tissue in a patient in need thereof, comprising: (a) debriding the chronic open wound; (b) topically applying to the chronic open wound a gel/jelly comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— $[CH_2—CH_2—O]_a$— $[CH_2—CH(CH_3)—O]_b$— $[CH_2—CH_2—O]_a$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of an anesthetic; (c) applying an occlusive bandage to the chronic open wound; (d) removing the occlusive bandage from the chronic open wound; and (e) debriding the chronic open wound.

In a third principal embodiment the invention provides a method of treating pain in a chronic open wound in non-mucosal tissue in a patient in need thereof, comprising: topically applying to the chronic open wound a gel/jelly comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— $[CH_2—CH_2—O]_a$— $[CH_2—CH(CH_3)—O]_b$— $[CH_2—CH_2—O]_a$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of an anesthetic.

The invention can further be understood with reference to various subembodiments which can modify any of the principal embodiments. These subembodiments can be combined in any manner that is both mathematically and physically possible to create additional subembodiments, which in turn can modify any of the principal embodiments.

Discussion of Dissolution Subembodiments

Any of the embodiments or subembodiments of the present invention can further be defined in terms of the dissolution characteristics of the topical dosage form. Thus, in various subembodiments the dosage form releases less than 75% of its lidocaine at 30 minutes and less than 90% of its lidocaine at 60 minutes when tested in a USP Apparatus 1 (paddle) at 50 rpm in 500 ml of an acetic acid/sodium acetate buffer, pH 4.0 at 32° C.

In other subembodiments the dosage form releases less than 60% of its lidocaine at 30 minutes and less than 75% of its lidocaine at 60 minutes when tested in a USP Apparatus 1 (paddle) at 50 rpm in 500 ml of an acetic acid/sodium acetate buffer, pH 4.0 at 32° C.

In still further subembodiments the dosage form releases less than 55% of its lidocaine at 30 minutes and less than 70% of its lidocaine at 60 minutes when tested in a USP Apparatus 1 (paddle) at 50 rpm in 500 ml of an acetic acid/sodium acetate buffer, pH 4.0 at 32° C.

Discussion of Formulation Subembodiments

Any of the embodiments or subembodiments of the current invention can further be understood in terms of the formulation use to make the topical dosage form.

One of the preferred characteristics of the dosage forms used in the methods of the present invention is their gel temperature. Thus, in various subembodiments the dosage form is characterized by a gel temperature that is between room temperature and the body temperature of the patient.

Thus, in one particular subembodiment the topical dosage form is an ointment or gel comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— $[CH_2—CH_2—O]_a$— $[CH_2—CH(CH_3)—O]_b$— $[CH_2—CH_2—O]$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of lidocaine.

The thickening agent is also an important component of the formulation, for ensuring the stability of the formulation and its utility in medical applications. The thickening agent preferably yields a clear formulation, yet is easily processed to produce a product with appropriate viscosity and handling characteristics. Suitable thickening agents include, for example, cellulose derivatives, natural gums, and inorganic compounds. More particular examples include methyl cellulose, hydroxyethyl cellulose, hydroxypropyl cellulose, alginates, guar gum, pectin, aluminum silicate, magnesium aluminum silicate, silica, and combinations thereof. A preferred thickening agent is xanthan gum, preferably from 0.1 to 2.5 weight parts, from 0.2 to 1.5 weight parts, most preferably 0.5 weight parts.

Other subembodiments are defined by the anesthetic chosen for the formulation, and the proportion of anesthetic chosen for the formulation. Suitable anesthetics include, for example, benzocaine, prilocaine, tetracaine, bupivacaine, lidocaine, and their pharmaceutically acceptable salts. A particularly preferred anesthetic is lidocaine, or one of its pharmaceutically acceptable salts.

These anesthetics can be present in any proportion equaling a therapeutically effective dose, but is preferably present in an amount of from 2.0 weight parts to 5.0 weight parts, with 3.0 to 4.5 weight parts or 4.0 weight parts being particularly preferred, particularly for lidocaine.

The formulation can also include a preservative such as benzyl alcohol or can be provided sterilized without benzyl alcohol.

The formulations also benefit from the addition of a pH adjusting agent to prevent hydrolysis of the lidocaine. The pH of the formulations will preferably be from 3 to 6 adjusted with the pH adjusting agents or buffers. A preferred pH adjusting agent is citrate buffer, preferably from 25 to 100 mM. Alternative buffers are well known in the art and include, for example, acetate and phosphate buffers.

The formulations are aqueous-based formulations, preferably containing from 70 to 90 weight parts water, more preferably from 70 to 80 weight parts of water. The water used in the formulations is of a pharmaceutically acceptable grade. It is also possible to substitute various humectants for the water, such as glycerine, glycerol and polyethylene glycol, in amounts preferably between 5 and 15 weight parts. Thus, while the formulations of the present invention commonly contain from 70 to 90 weight parts of water, they may also contain from 55 to 85 weight parts water and from 5 to 15 weight parts of a humectant such as glycerine, glycerol, or polyethylene glycol, wherein the total weight parts of water and humectant preferably add up to from 70 to 90 weight parts.

The formulations may be based upon a copolymer. A preferable copolymer is a poloxamer having an ethylene oxide/n-propylene oxide block polymer structure, random or ordered. The ethylene oxide preferably may be in molar excess to the n-propyl oxide, and the ratio of ethylene oxide to n-propyl oxide units (i.e. a:b) may be from 2:1 to 4:1. The preferable block copolymer having the structure of HO—[CH$_2$—CH$_2$—O]$_a$—[CH$_2$—CH(CH$_3$)—O]$_b$—[CH$_2$—CH$_2$—O]$_a$—H. The structure consists of a hydrophobic central core of propylene oxide (represented by "b" in the above figure), flanked by hydrophilic ethylene oxide (represented by "a" in the above figure) on both sides. The molecular weight of the copolymer may be from 5000 to 25000. In some instances, the molecular weight of the copolymer may be from 9000 to 16000. The sum of the two a's preferably is from 50 to 500, from 100 to 300, from 150 to 250, or most preferably 200. b is preferably from 30 to 100, from 50 to 80, from 60 to 70, or most preferably 65. The ratio of the 2 a's to b is preferably from 2:1 to 4:1. The formulation preferably is from 10 to 20 weight parts of the copolymer.

The formulation may also be defined by several chemical characteristics, including a gel temperature that is between room temperature and the body temperature of a patient, e.g., 37° C. The formulation may have a viscosity at room temperature of from 200,000 to 500,000 cps, more preferably from 100,000 to 1,000,000 cps. In addition, the formulation may include no component other than the above described that may change the viscosity of the pharmaceutical formulation at room temperature (i.e. by more than 100,000, 50,000 or 10,000 cps).

Methods of Treatment

The formulations of the present invention can be used in any method that topical anesthetics have historically been used, although they have particular utility in lidocaine applications. The formulations have been found effective for inducing local anesthesia on the chronic open wounds which cause pain. The formulations induce local anesthesia, and they do so without inducing significant irritation.

Thus, in various subembodiments the invention provides a method for the treatment of debridement pain. In further subembodiments the invention provides a method of treating pain in a chronic open wound in non-mucosal tissue, such as skin, in a patient in need thereof, comprising debriding the chronic open wound, topically applying to the chronic open wound a gel/jelly or ointment comprising the dosage form of the present invention, applying an occlusive bandage to the chronic open wound, removing the occlusive bandage from the chronic open wound, and debriding the chronic open wound. Preferably, the removal step occurs at least 24, 48, 72 hours, 96 hours or 120 hours after the applying the gel/jelly or ointment to effectively reduce pain arising from the removal step.

In still further subembodiments the invention provides a method comprising topically applying a gel/jelly or ointment to the debrided open wound and applying an occlusive bandage to the debrided open wound.

In particularly preferred subembodiments the methods are used to treat pain, particularly debridement pain, in non-mucosal tissue such as skin. Thus, in additional subembodiments the methods are used to treat pain, particularly debridement pain, in venous leg ulcers, diabetic leg/foot ulcers, abdominal wounds, vasculitic ulcers, abrasions, burns and pressure ulcers. As noted in this document, the subembodiments are useful for treating debridement pain arising more than 24, 48, 72 hours, 96 hours or 120 hours after the application of the dosage form.

The invention provides a method to use a Numeric Rating Scale (NRS) to report pain relief.

Methods of Manufacture

The formulations of the present invention can be manufactured using conventional manufacturing techniques as described, for example, in REMINGTON: THE SCIENCE AND PRACTICE OF PHARMACY (22d edition), although several discoveries have been made to improve their manufacture.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Example Pharmaceutical Formulation

The table below illustrates an example of pharmaceutical formulation of the present invention. The table below is purely exemplary of the invention and is not intended to limit the scope of what the inventors regard as their invention. Unless indicated otherwise, parts are parts by weight.

TABLE 1

Example Pharmaceutical Formulation

| Raw material | 1A<br>% (w/w) | 1B<br>% (w/w) |
|---|---|---|
| Poloxamer F127, USP | 16.00 | 16.00 |
| Xanthan gum, USP | 0.50 | 0.50 |
| Lidocaine HCl, USP | 4.00* | 4.00* |
| Citric acid monohydrate, USP | 0.39 | 0.39 |
| Sod. citrate dihydrate, USP | 0.93 | 0.93 |
| Benzyl alcohol, USP | 1.00 | — |
| Purified Water, USP qs | 77.18 | 78.18 |
| Total | 100.00 | 100.00 |

*excluding waters of hydration; based on weight of salt

Example 2. Effectiveness of Treatment

In an attempt to relieve pain in patients with chronic open wounds and to reduce the number of narcotic medications prescribed, patients were treated with one direct application of ~5 mL of the gel/jelly containing 4% lidocaine in TRI-726 matrix (MP-601gel). The evaluation included 33 patients consisting of 14 men (42%) and 19 women (58%) suffering from pain due to chronic open wounds. The age range of the patients was from 53 to 89 years old. 12 patients had venous leg ulcers (36%), 11 had diabetic foot ulcers (33%), 4 had pressure ulcers (12%), 2 had vasculitic ulcers (6%), 2 had a traumatic wound (6%), 1 had an abdominal wound (3%), and 1 had a second-degree burn (3%) (Table 2). The pain was rated by the patient prior to the application of MP-601 gel on a Numeric Rating Scale (NRS), a commonly used method to assess pain and stress, graduating from 0="no pain" to 10="worst imaginable pain". The duration of the pain relief and the time until the patient felt that MP-601 gel was no longer effective were calculated from these scores. The pain information was collected at a return visit the next week, which was maintained in a patient diary. The patients continuously wore standard dressings and bandages appropriate for the wound types during the evaluation.

TABLE 2

Types of Chronic Open Wound in Patients

| Types of Wound | Number | Percentage (%) |
|---|---|---|
| Venous Leg Ulcer | 12 | 36.4 |
| Diabetic Foot Ulcer | 11 | 33.3 |
| Pressure Ulcer | 4 | 12.1 |
| Vasculitic Ulcer | 2 | 6.1 |
| Traumatic Wound | 2 | 6.1 |
| Abdominal Wound | 1 | 3.0 |
| Second-Degree Burn | 1 | 3.0 |

Table 3 shows the initial pain scale/score in the patients prior to the application of MP-601 gel. 6 patients recorded pain 10 "worst imaginable pain" (18%), 24 patients indicated 6 or more in the pain scale (72%), and no patients recorded 0 "no pain", which suggests that the participating patients suffered from the severity of pain accompanied by their chronic wounds.

TABLE 3

Initial Pain Scale of Chronic Wound by Patients

| Pain Scale | 1 | 2 | 3 | 4 | 5 | 6 | 7 | 8 | 9 | 10 |
|---|---|---|---|---|---|---|---|---|---|---|
| Number of Patient Recorded | 0 | 0 | 1 | 3 | 5 | 1 | 7 | 6 | 4 | 6 |
| Percentage | 0 | 0 | 3.0 | 9.1 | 15.2 | 3.0 | 21.2 | 18.2 | 12.1 | 18.2 |

Table 4 shows the duration of the pain relief over one week after the application of MP-601 gel. Of all patients, 2 patients had no pain relief (6%) or were non-responsive to lidocaine. Of the 31 responders who reported an improvement, all recorded that they felt pain relief by day 1. Approximately 94% of the responders continued to feel pain relief by day 2. The result shows that MP-601 gel was effective in providing pain relief up to 48 hours after one application. The product was effective in complete resolution of pain in the majority of patients for that period of time. Over half of the responders (58%) reported the effectiveness of the M-601 gel lasted up to 4 days, which is more than expected and cannot be easily explained. However, the efficacy of M-601 gel to yield therapeutic benefits is provided.

TABLE 4

Duration of Pain Relief

| | 1 Day | 2 Days | 3 Days | 4 Days | 5 Days | 6 Days | 7 Days |
|---|---|---|---|---|---|---|---|
| All Patients (33) | 94% | 88% | 73% | 55% | 21% | 15% | 6% |
| All Responders (31) | 100% | 94% | 77% | 58% | 23% | 16% | 7% |

FIG. 1 shows the average pain score reported by the patients over one week following the application of MP-601 gel. MP-601 gel was applied once on day 0. The average pain scores from day 1 to day 4 were statistically significantly lower $p<0.01$) compared to the baseline (day 0) and from day 5 to day 7 scores.

Figure 2:
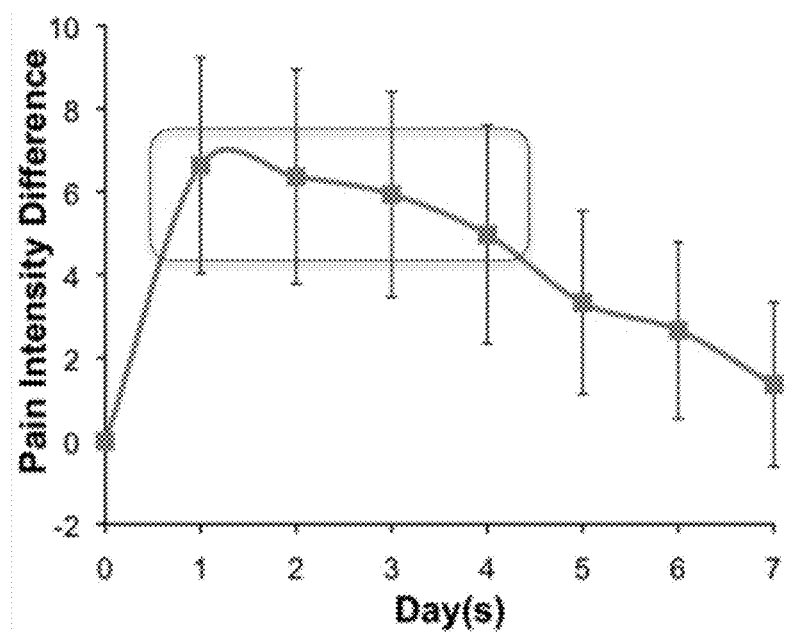
FIG. 2 shows the change in pain intensity difference (NRS pain scores normalized to baseline) over one week after the application of MP-601 gel, as reported in Example 2.

FIG. 2 shows the average pain intensity difference (pain scores normalized to baseline value) over one week following the application of MP-601 gel. MP-601 gel was applied once on day 0. The average pain intensity differences from day 1 to day 4 were statistically significantly lower $p<0.01$) compared to the baseline (day 0) and from day 5 to day 7 scores.

Table 5 shows a comparison of the average pain scale/score prior to and at one week after the application of MP-601 gel. The average pain scale/score of all patients was 7.2 prior to the application and 6 at one week after the application. Among the responders reporting an improvement, the average pain scale was 7 prior to the application and 5.8 at one week after the application. The table demonstrates that the pain experienced by the enrolled patients was lower even at one week than they experienced at the beginning of the study.

TABLE 5

Comparison of Average Pain Scale/score before
and at One Week After MP-601 Application

| | Beginning of Study | End of Study |
|---|---|---|
| All | 7.2 | 6 |
| Responders | 7 | 5.8 |

Patients' comfort level and acceptance of MP-601 were very high throughout the study. No adverse reactions were reported during the entire study period.

Example 3. Dissolution Testing of Representative Formulation

The formulation of Example 1 with 4% lidocaine was tested for its dissolution properties and compared to the dissolution profiles for Aster™ (Gensco Pharma, Miami, Florida) and Regenecare™ (MPM Medical, Inc., Irving, Texas). Testing was performed in a USP Apparatus 1 (paddle) at 50 rpm in 500 ml of an acetic acid/sodium acetate buffer, pH 4.0 at 32° C. The testing was performed according to bioequivalence recommendations published by the United States Food and Drug Administration for lidocaine topical patch as of Oct. 3, 2017, except that a USP Apparatus 1 was used, and the gel for each product was filled into size 00 hard gelatin capsules and placed in sinkers prior to testing.

Figure 3:
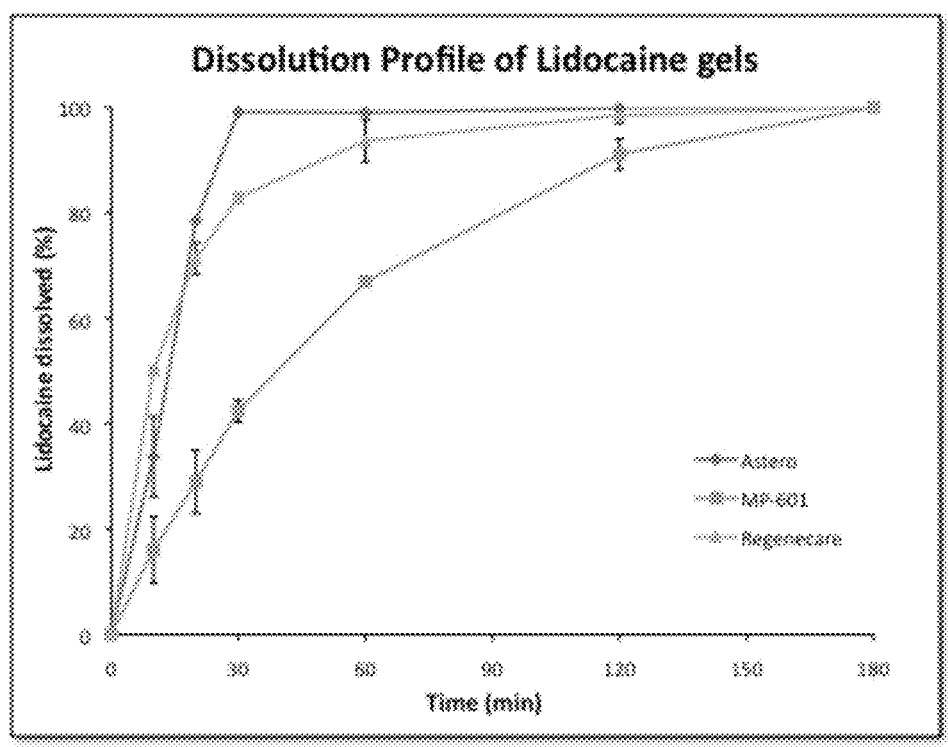
FIG. 3 reports the dissolution profile of an exemplary formulation of the present invention compared to two commercially available formulations, Astero™ (Gensco Pharma, Miami, Florida) and Regenecare™ (MPM Medical, Inc., Irving, Texas).

The results are reported in Table 6 and depicted in FIG. 3.

TABLE 6

| Time | Astero ™ | MP-601 | Regenecare ™ |
|---|---|---|---|
| 0 | 0 | 0 | 0 |
| 10 | 33.7399 | 16.0242 | 50.2084 |
| 20 | 78.5086 | 28.9541 | 71.2818 |
| 30 | 99.0963 | 42.3929 | 82.8594 |
| 60 | 98.9944 | 66.896 | 93.6216 |
| 120 | 99.8551 | 91.0855 | 98.4742 |
| 180 | 100 | 100 | 100 |

Other Embodiments

In further embodiments, the invention is described as follows:

(1) A method of treating pain comprising applying to an open wound a topical dosage form comprising from 2 to 5% lidocaine, wherein said dosage form releases less than 75% of its lidocaine at 30 minutes and less than 90% of its lidocaine at 60 minutes when tested in a USP Apparatus 1 (paddle) at 50 rpm in 500 ml of an acetic acid/sodium acetate buffer, pH 4.0 at 32° C.

(2) A method of treating pain in a chronic open wound in non-mucosal tissue in a patient in need thereof, comprising: (a) debriding the chronic open wound; (b) topically applying to the chronic open wound an ointment or gel comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— [CH2—CH2—O]a-[CH$_2$—CH(CH$_3$)—O]b-[CH$_2$—CH$_2$—O]$_a$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of an anesthetic; (c) applying an occlusive bandage to the chronic open wound; (d) removing the occlusive bandage from the chronic open wound; and (e) debriding the chronic open wound.

(3) A method of treating pain in a chronic open wound in non-mucosal tissue, comprising: (a) topically applying to the chronic open wound an ointment or gel comprising: (i) from 70 to 90 weight parts of water or a mixture of water and a humectant selected from glycerine, glycerol, polyethylene glycol, and combinations thereof; (ii) from 10 to 25 weight parts of a copolymer having the following block structure: HO— [CH2—CH2—O]a-[CH2—CH(CH3)—O]b-[CH2—CH2—O]$_a$—H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of an anesthetic.

(4) The method of embodiment 2 or 3 wherein said dosage form releases less than 75% of its lidocaine at 30 minutes and less than 90% of its lidocaine at 60 minutes when tested in a USP Apparatus 1 (paddle) at 50 rpm in 500 ml of an acetic acid/sodium acetate buffer, pH 4.0 at 32° C.

(5) The method of any of the preceding embodiments, wherein said dosage form releases less than 60% of its lidocaine at 30 minutes and less than 75% of its lidocaine at 60 minutes when tested according to claim 1.

(6) The method of embodiments 1, 3, 4, or 5, further comprising: (a) topically applying the ointment or gel to the debrided open wound; and (b) applying an occlusive bandage to the debrided open wound.

(7) The method of embodiments 1, 3, 4, or 5, further comprising: (a) debriding the chronic open wound prior to applying said dosage form; (b) applying an occlusive bandage to the chronic open wound after applying the dosage form; (c) removing the occlusive bandage from the chronic open wound; and (d) debriding the chronic open wound.

(8) The method of embodiments 2 or 7, wherein said removal step occurs at least 72 hours, 96 hours or 120 hours after the applying step (c), and the method is effective to reduce pain arising from said removal step.

(9) The method of any of the preceding embodiments, wherein said topical dosage form is an ointment or gel comprising: (i) from 70 to 90 weight parts of water, glycerine, glycerol or polyethylene glycol; (ii) from 10 to 25 weight parts of a copolymer having the following block structure: HO— [CH2—CH2—O]a-[CH2—CH(CH3)-O]b-[CH2—CH2—O]a-H, wherein the ratio of a:b is from 2:1 to 4:1, and the molecular weight of said copolymer is from 9000 to 16000; (iii) from 0.1 to 3.0 weight parts of xanthan gum; and (iv) from 2.0 to 5.0 weight parts of lidocaine.

(10) The method of any of embodiments 2, 3, or 4, wherein the anesthetic is lidocaine or a pharmaceutically acceptable salt thereof.

(11) The method of any of embodiments 2, 3, or 9, wherein the dosage form includes from 10 to 20 weight parts of said copolymer.

(12) The method of any of embodiments 2, 3, or 9, wherein said copolymer is a poloxamer.

(13) The method of any of embodiments 2, 3, or 9, wherein the sum of a's in the block structure of the copolymer equals 200, and b in the block structure has a value of 65.

(14) The method of any of embodiments 2, 3, or 9, wherein the dosage form includes from 0.1 to 2.5 weight parts of said xanthan gum.

(15) The method of any of the preceding embodiments for the treatment of debridement pain.

(16) The method of any of the preceding embodiments, wherein the topical dosage form comprises from 2.0 to 4.5 weight parts lidocaine or a pharmaceutically acceptable salt thereof based on the weight of the free base.

(17) The method of any of the preceding embodiments, wherein the topical dosage form comprises about 4.0 weight parts lidocaine or a pharmaceutically acceptable salt thereof based on the weight of the free base.

(18) The method of any of the preceding embodiments, wherein the dosage form further comprises benzyl alcohol.

(19) The method of any of the preceding embodiments, wherein the dosage form includes a buffer selected from a citrate buffer, an acetate buffer, and a phosphate buffer.

(20) The method of any of the preceding embodiments, wherein the dosage form includes from 25 to 100 mM of a citrate buffer.

(21) The method of any of the preceding embodiments, wherein the dosage form includes from 70 to 80 weight parts of water.

(22) The method of any of the preceding embodiments, wherein the dosage form is characterized by a gel temperature that is between room temperature and the body temperature of the patient.

(23) The method of any of the preceding embodiments, wherein the dosage form has a viscosity at room temperature of from 100,000 to 1,000,000 cps.

(24) The method of any of the preceding embodiments, wherein the dosage form contains no other component that changes the viscosity of the liquid at room temperature by more than 100,000 cps.

(25) The method of any of embodiments 1, 5, 6, 7, 8 or 9, wherein the chronic open wound is in non-mucosal tissue.

(26) The method of embodiments 2, 3, or 24, wherein the chronic open wound is selected from the group consisting of venous leg ulcers, diabetic leg ulcers, abdominal wounds, vasculitic ulcers, abrasions, burns and pressure ulcers.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Lok, et al. "EMLA cream as a topical anesthetic for the repeated mechanical debridement of venous leg ulcers: A double-blind, placebo-controlled study", Journal of the American Academy of Dermatology, 1999; 40(2) Part 1:208-213.

Powers, et al., "Wound healing and treating wounds: Chronic wound care and management", Journal of the American Academy of Dermatology, 2016; 74(4); 607-625.

http://www.diabetes.org/diabetes-basics/statistics/Hoffman D., et al., "Pain in venous leg ulcers." 1997, Journal of Wound Care, 6(5):222-224.

Phillips T., et al., "A study of the impact of leg ulcers on quality of life: financial, social, and psychologic implications." J Am Acad Dermatol. 1994 Jul. 31(1):49-53.

Terry Treadwell, M D., et al., "Treatment of Pain in Wounds with a Topical Long Acting Lidocaine Ointment." 2014.

Price P E, Fagervik-Morton H, Mudge E J, et al., "Dressing-related pain, in patients with chronic wounds: an international patient perspective." Int Wound J., 2008; 5(2):159-171.

Woo K Y, Coutts P M, Price P, Harding K, Sibbald R G., "A randomized crossover investigation of pain at dressing change comparing 2 foam dressings." Adv Skin Wound Care. 2009; 22(7):304-310.

http://www.wisegeekhealth.com/what-is-the-difference-between-lidocaine-and-benzocaine.htm http://www.ehow.com/about_5398369_lidocaine-vs-benzocaine.html Michael F. Powell, "Stability of Lidocaine in Aqueous Solution: Effect of Temperature, pH, Buffer, and Metal Ions on Amide Hydrolysis", Pharmaceutical Research, February 1987; 4(1):42-45.

The invention claimed is:

1. A topical dosage form comprising:
a) from 2 to 5% lidocaine or a pharmaceutically acceptable salt thereof:
b) from 70 to 90 weight parts of water or a mixture of water and a humectant selected from glycerine, glycerol, polyethylene glycol, and combinations thereof;
c) from 10 to 25 weight parts of a copolymer having the following block structure:

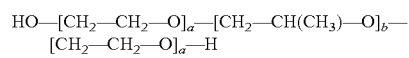

wherein the ratio of a:b is from 2:1 to 4:1, and the molecular weight of said copolymer is from 9000 to 16000; and
d) 0.2-1.5 weight parts of xanthan gum.

2. The topical dosage form of claim 1 wherein said topical dosage form releases less than 75% of its lidocaine at 30 minutes and less than 90% of its lidocaine at 60 minutes when tested in a USP Apparatus 1 (paddle) at 50 rpm in 500 ml of an acetic acid/sodium acetate buffer, pH 4.0 at 32° C.

3. The topical dosage form of claim 1 wherein said topical dosage form provides pain relief for 48 hours following a single application.

4. The topical dosage form of claim 2 wherein said topical dosage form releases less than 60% of its lidocaine at 30 minutes and less than 75% of its lidocaine at 60 minutes when tested in a USP Apparatus 1 (paddle) at 50 rpm in 500 ml of an acetic acid/sodium acetate buffer, pH 4.0 at 32° C.

5. The topical dosage form of claim 1 in a kit, further comprising instructions to:
a) debride an open wound;
b) topically apply the topical dosage form to the debrided open wound; and
c) applying an occlusive bandage to the debrided open wound.

6. The topical dosage form of claim 1 wherein said topical dosage form includes from 10 to 20 weight parts of said copolymer.

7. The topical dosage form of claim 1 wherein said copolymer is a poloxamer.

8. The topical dosage form of claim 1 wherein the sum of a's in the block structure of the copolymer equals 200, and b in the block structure has a value of 65.

9. The topical dosage form of claim 1 wherein said topical dosage form comprises from 2.0 to 4.5 weight parts lidocaine or a pharmaceutically acceptable salt thereof based on the weight of the free base.

10. The topical dosage form of claim 1 wherein said topical dosage form comprises about 4.0 weight parts lidocaine or a pharmaceutically acceptable salt thereof based on the weight of the free base.

11. The topical dosage form of claim 1 wherein said topical dosage form is characterized by a gel temperature that is between room temperature and the body temperature of the patient.

* * * * *